United States Patent [19]
Luttrell et al.

[11] Patent Number: 5,144,943
[45] Date of Patent: Sep. 8, 1992

[54] DYNAMIC ANKLE SPLINT

[75] Inventors: Tammy C. Luttrell, Elbert, Colo.; Eugene G. Crepeau, Albuqureque, N. Mex.

[73] Assignee: O-Motus, Inc., Colorado Springs, Colo.

[21] Appl. No.: 550,256

[22] Filed: Jul. 9, 1990

Related U.S. Application Data

[63] Continuation-in-part of Ser. No. 495,044, Mar. 16, 1990, and a continuation-in-part of Ser. No. 507;212, Apr. 9, 1990.

[51] Int. Cl.$^5$ .............................................. A61H 1/02
[52] U.S. Cl. .................................. 128/25 B; 602/27
[58] Field of Search ............... 128/25 R, 25 B, 52, 128/49, 80 H, 80 E, 80 J; 602/27, 28

[56] References Cited

U.S. PATENT DOCUMENTS

| | | | |
|---|---|---|---|
| 246,984 | 9/1881 | Stillman | 128/80 H |
| 2,439,100 | 4/1948 | Richards | 128/80 E |
| 3,086,522 | 4/1963 | Frohmader | 128/80 J |
| 4,351,527 | 9/1982 | Crisp, Jr. | 272/141 X |
| 4,751,917 | 6/1988 | Ruf | 128/25 R |
| 4,795,148 | 1/1989 | Rangaswamy | 128/25 B |

FOREIGN PATENT DOCUMENTS

| | | | |
|---|---|---|---|
| 1454461 | 1/1989 | U.S.S.R. | 128/80 H |
| 8802249 | 4/1988 | World Int. Prop. O. | 128/25 B |

*Primary Examiner*—Robert Bahr
*Assistant Examiner*—J. Doyle
*Attorney, Agent, or Firm*—Beaton & Swanson

[57] ABSTRACT

A method and apparatus for increasing the mobility of the ankle joint by application of a continuous or cycled force between the lower leg and anterior portion of the heel. In a preferred embodiment, an expandable cylinder is pivotally attached to a heel cup and to a lower leg cuff. A selected and quantifiable force is applied between the heel cup and lower leg cuff by a slidable expansion of concentric sleeves within the expandable cylinder using a coiled spring.

30 Claims, 3 Drawing Sheets

DYNAMIC ANKLE SPLINT

This is a continuation-in-part of application No. 494,044, filed Mar. 16, 1990, pending, and application No. 507,212, filed Apr. 9, 1990, pending.

BACKGROUND OF THE INVENTION

A loss of joint flexibility is experienced by individuals recovering from neuromuscular diseases, traumatic injuries such as bone fractures, tendon and ligament tears, joint replacements and burns. In order to regain joint flexibility, it is necessary to flex or extend the joint in a repeated, controlled and quantifiable manner. It is also sometimes necessary to apply a relatively small force of a long duration or repeatedly to resolve immobilization stiffness and established contractures regardless of etiology.

Devices have been developed for either flexing or extending joints in a single plane. Examples of these devices are in U.S. Pat. Nos. 4,508,111, 4,397,308, 4,485,808 and 4,538,600, all by Hepburn. These devices generally comprise upper and lower struts which attach to the limbs of the desired joint using an appropriate attachment means such as VELCRO or strapping. The upper and lower struts are pivotally attached to one another at the ends adjacent the joint. The pivotal attachment includes a cylindrical housing with a cam, wherein one of the struts is attached to the cam and the other bears on the cam surface through a bearing spring. Flexing or extending the joint causes a corresponding approximation or alignment of the struts relative to one another and a compression or expansion of the spring. The use of the spring allows a somewhat quantifiable and adjustable constant force to be applied to urge the flexing or extending of the joint.

The devices described in the patents named above are a great advance in that they apply a flexing or extending force on the joint rather than simply immobilizing the joint, but they have several drawbacks. One drawback is that they do not provide for cycled flexing and extending. Recently, it has been found that cycled motion is more therapeutic than static force for treating total joint replacements and in many other therapies. Another drawback is that they pivot at a single fixed axis and move through a single plane. In contrast, the normal motion of most body joints includes pivoting at an axis that slides in relation to the joint to produce a "component motion" and that moves through at least three planes in a "triplanar motion." For example, the human knee joint does not pivot at a single axis. Instead, it pivots at an axis that slides around the femur, so that the lower leg actually moves away from the upper leg as the knee bends. A similar situation exists in the elbow, ankle and many other joints. The failure to accommodate this movement causes a binding of the pivot mechanism of the device, destructive pressure on the internal body joint-bearing surfaces, and migration and misalignment of the device. Accommodating this movement is particularly difficult because, not only is it complex, it also varies greatly from patient to patient.

Other devices exist which do accommodate component motion to allow normal joint response, but these devices are merely braces to limit the range of joint motion. An example of such a device is in U.S. Pat. No. 4,489,718 by Martin. This device may support the knee joint effectively and allow for limited knee motion, but it does not apply any flexing or extending force to rehabilitate the knee and increase flexibility.

The ankle joint is especially challenging to the physical therapist because of the frequency of injury and the complexity of movement. The anterior tibiotalar ligament and other parts of the deltoid ligament are particularly prone to spraining or tearing, typically caused by the foot being forced into external rotation and eversion with respect to the leg. Once the initial trauma has subsided and the patient is able to mobilize the joint, gradual and repeated stretching and stressing of the injured area may be indicated to restore strength and mobility.

Regarding the complexity of movement of the ankle joint, it is well known that movement of the foot with respect to the ankle involves much more than a simple pivoting of the foot about an axis at the junction between the foot an lower leg. Instead, a large variety of movements and combinations of movements are essential. Eversion and inversion refer to movement of the foot about a horizontal axis on the sagittal plane. Abduction and adduction are the movement of the forefoot about a vertical axis. Internal and external rotation are the movement between the leg and hindfoot occurring about a vertical axis. Plantarflexion and dorsiflexion are movement about a horizontal axis lying in the frontal plane which results in vertical movement of the calcaneus. Pronation and supination are functional movements occurring around the obliquely situated subtalar or transverse tarsal joint axis. Because these axes are inclined backward, downward and laterally, pronation and supination also necessarily cause some abduction and adduction, inversion and eversion, and plantarflexion and dorsiflexion. Each of these movements may involve various movements of joint elements with respect to one another, including swing, rotation, spin, roll, slide, and distraction and compression.

Given the complexities of ankle joint movement, it can be seen that attempting to mobilize the joint with a simple pivoting about a horizontal axis will not be effective. In fact, it may be counterproductive because it may cause unnatural straining, compression and distraction of joint elements by preventing the necessary ancillary component movements.

SUMMARY OF THE INVENTION

The present invention is a dynamic splint for supporting and actively and passively mobilizing the ankle joint, while accommodating any joint component movements. The mechanism may be utilized to apply a selected force in a gradual and continuous manner or in a discrete and cyclical manner. The mechanism operates on the heel, and is adjustable for either flexing or extending of the heel as desired.

In a preferred embodiment of the invention, the patient's heel is placed in a heel cup. The heel cup is attached to a ball and socket joint. The ball and socket joint, in turn is attached to a force-applying element such as a spring-filled cylinder arrangement. The cylinder arrangement is attached to the lower leg with a releasable leg cuff or equivalent attachment means.

In operation the spring-filled cylinder exerts a continuous passive force between the lower leg and the calcaneus. The direction of this force urges the heel either upward or downward, depending on the configuration of the spring-filled cylinder for the chosen mode of operation, in order to cause dorsiflexion or plantarflexion along with ancillary component movements. The ball and socket joint which carries the force between the lower leg portion and the heel portion of the apparatus allows the heel and therefore the entire foot to move in the path of least resistance in order to allow normal articulation to occur at the individual joint surfaces. By placing the force-applying mechanism behind the foot and applying the force to the ankle through a heel cup, the mechanism achieves a mechanical advantage to lever the heel to overcome the gastroc/soleus muscle.

The invention can also be utilized to brace the ankle joint to allow the patient to put weight on the foot and allow a predetermined extent of mobility of the joint, but not to the extent causing pain or trauma. It can also be used to hold the joint in a desired position, such holding the calcaneus in a downward position to allow the patient to walk and swing the foot without striking the toes.

In another embodiment of the invention, the force applied by the spring-filled cylinder between the lower leg and the heel may be cycled in a selected manner to cause repeated and controlled flexing and extending of the ankle joint. The cycling may be accomplished with a suitable drive means such as a programmable stepper motor engaged with a threaded shaft and a microswitch or potentiameter to reverse the direction at desired levels of flexing and extending.

DESCRIPTION OF THE INVENTION

Figure 1:
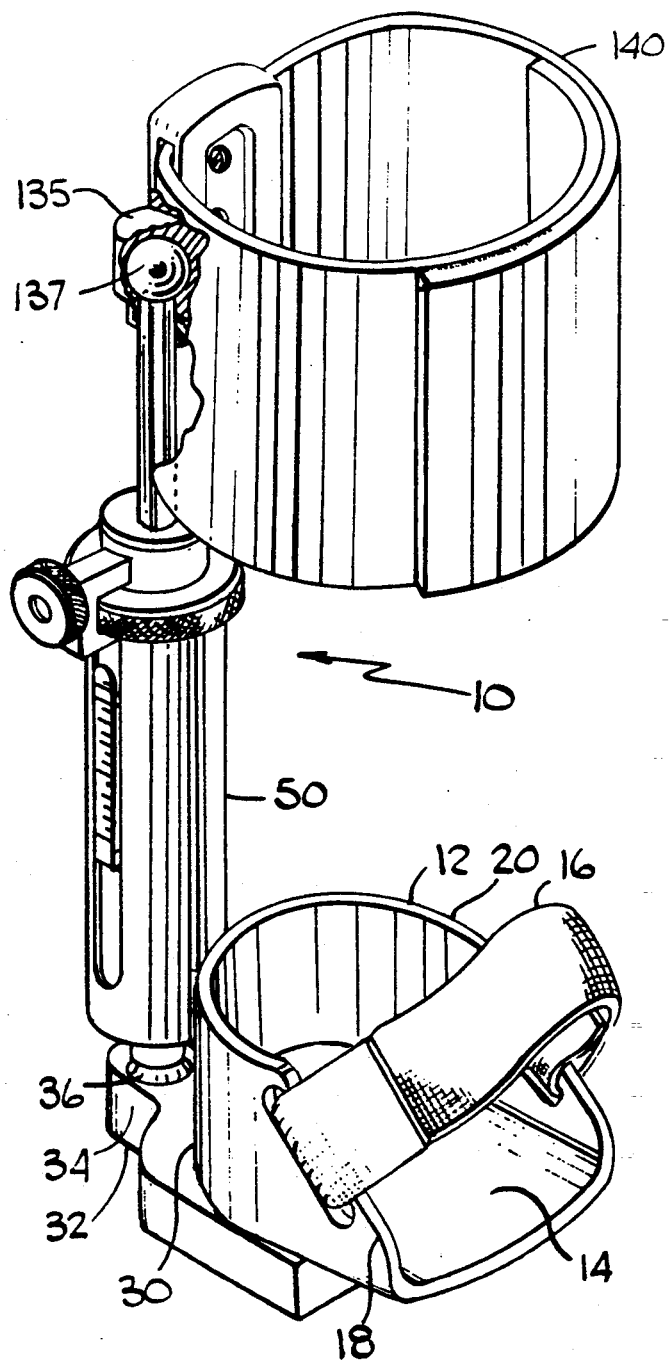
FIG. 1 shows a perspective view of a preferred embodiment of the invention.

FIG. 1 shows a perspective view of a preferred embodiment of the present invention, for use in applying a continuous force to mobilize the ankle joint. The principal elements of the apparatus 10 are a heel cup 12, a lower ball 36 and lower socket 34, an expandable cylinder portion 50, an upper ball 137 and upper socket 135, and a lower leg cuff 140. These and the other components are described in detail below.

The heel cup 12 has a suitable surface 14 to receive a patient's heel such as the cup-shaped interior shown in FIG. 1. The heel cup 12 may be fabricated from plastic or any other relatively rigid material that will attach securely to the heel. The heel cup 12 is attached to the heel by means of adjustable VELCRO straps 16 which extend around the front of the ankle from one heel cup lip 18 to the other heel cup lip 20. Attached to the posterior 30 of the heel cup 12 is a heel cup bracket 32 which holds a lower socket 34. The lower socket 34 receives a lower ball 36 which is attached to and integral with a lower shaft 38 as best seen in the partial sectional view of FIG. 2.

Figure 5:
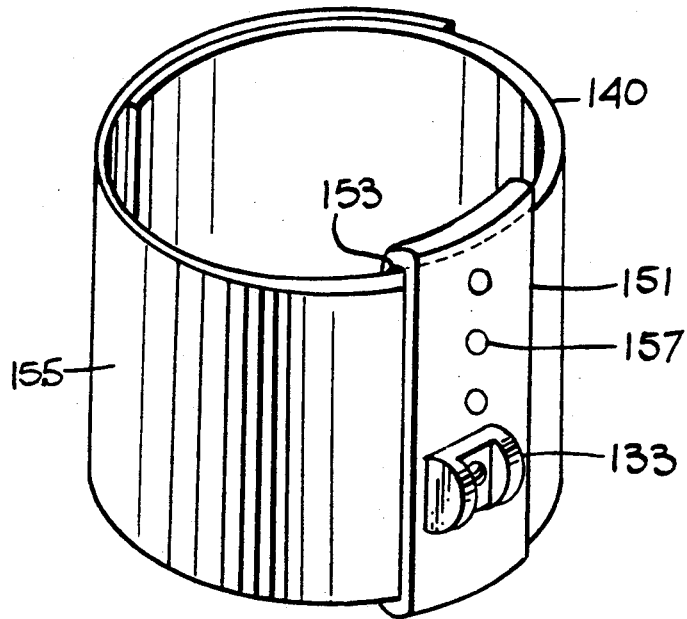
FIG. 5 shows an elevational view of the other embodiment with a partial sectional view of the spring-filled cylinder and piston configured for exerting a force urging the lower leg and heel apart.

As shown in FIG. 5, the lower leg cuff 140 may be a lower leg plate 151 with a slot 153 to receive a strap 155 releaseably attached to itself with VELCRO, buckling or other suitable attachment means. Adjustably attached to the posterior 131 of the lower leg cuff 140 is a lower leg cuff bracket 133 which holds an upper socket 135 which receives an upper ball 137 which is attached to and integral with an upper shaft 139. The adjustment is achieved by means of a plurality of mounting holes 157 for attachment of the bracket 133. The upper ball 137 and lower ball 36 and upper socket 135 and lower socket 34 allow pivoting of the lower leg cuff 140 and heel cup 12 about any axis. Moreover, it can be seen that the pivoting axis can change in any direction as the range of movement is effectuated, as described in more detail below.

Figure 2:
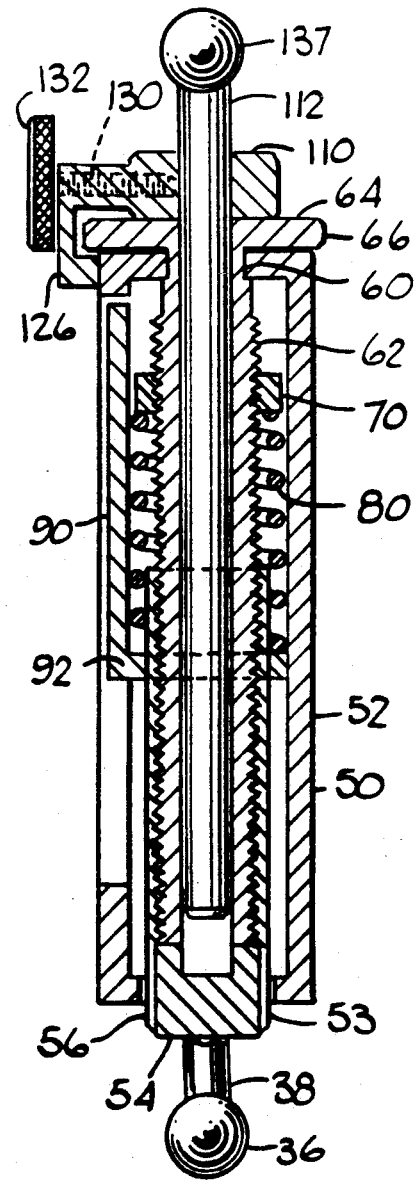
FIG. 2 shows a sectional view of the spring-filled cylinder of the preferred embodiment configured for exerting a force urging the lower leg and heel apart.
Figure 3:
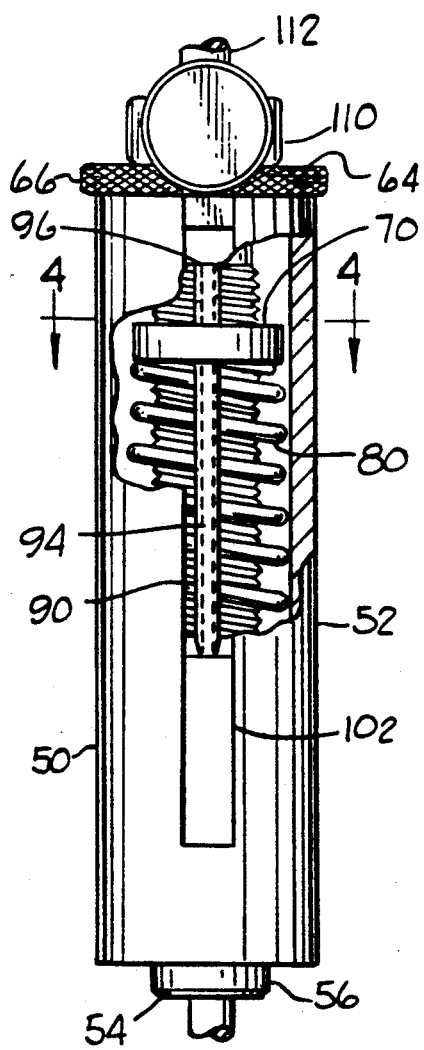
FIG. 3 shows an elevation view and partial sectional view of the preferred embodiment, showing the configuration of the force-measuring scale.

The lower shaft 38 extends from the lower ball 36 to the bottom of the expandable cylinder portion 50 as shown in FIG. 2. The expandable cylinder portion 50 includes an outer hollow cylinder 52 which has a bottom hole 53 which slidably receives a hollow sleeve 56 which extends axially through the bottom hole and part way through the interior of the hollow cylinder 52. The hollow sleeve is closed with a bottom plug 54 to which the lower shaft 38 is attached. Therefore, it can be seen that the lower ball 36, the bottom plug 54 and the hollow sleeve 56 are all attached to one another and move in unison when the hollow sleeve slides in and out of the bottom hole 53 of the hollow cylinder 52.

Figure 4:
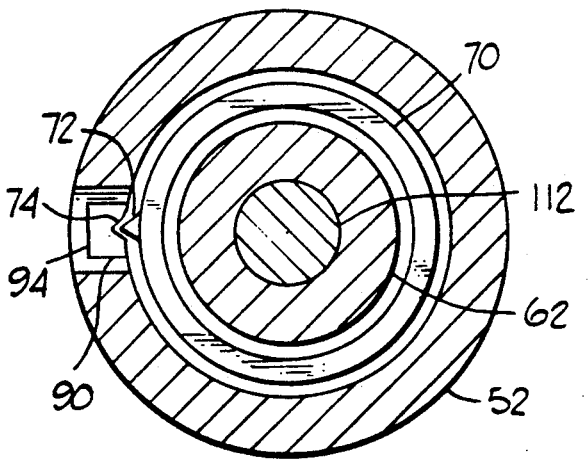
FIG. 4 shows a perspective view of another embodiment of the invention.

A scale 90 is attached to the exterior surface of the hollow sleeve 56. The scale 90 has an spring stop portion 92, the function of which is described below, extending radially from the hollow sleeve 56. The scale 90 also has a read-out portion 94 extending axially from the spring stop portion 92 to a terminal end 96. The read-out portion 94 nests in a window 102 of the hollow cylinder 52 as shown in FIG. 4, so that the readout portion is visible through the window when the expandable cylinder portion 50 is assembled.

At the top of the hollow cylinder 52, is a top end hole 60. The top end hole 60 receives a threaded sleeve 62 which extends from the top end hole 60 through the length of the hollow cylinder 52. The lower portion of the threaded sleeve 62 slides inside the hollow sleeve 56 and is contained therein. The upper end of the threaded sleeve 62 is attached to an adjusting wheel 64 which is external to and rests on the top end of the hollow cylinder 52. Manual rotation of the adjusting wheel 64 causes corresponding rotation of the threaded sleeve 62. The adjusting wheel 64 may include a knurled periphery 66 to facilitate such manual rotation. The adjusting wheel and attached threaded sleeve 62 are prevented from sliding out of the hollow cylinder 52 by a clamping collar 110 on top of the adjusting wheel 64, which also clamps the upper shaft 112 in the manner described below.

A threaded ring 70 is threaded onto the threaded sleeve 62 on the portion of the threaded sleeve that is not contained in the hollow sleeve 56 and is between the top end of the hollow sleeve 56 and the interior top end surface of the hollow cylinder 56. As shown in FIG. 4, the threaded ring 70 has a tab 72 extending from top to bottom. The tab 72 engages a longitudinal slot 74 in the interior surface of the hollow cylinder read-out portion 94 of the scale 90 to prevent any rotation of the threaded ring.

A coil spring 80 is positioned over the hollow sleeve 56 and threaded sleeve 62 in the space between those sleeves and the interior surface of the hollow cylinder 52. One end of the coil spring 80 bears against the lower surface of the threaded ring 70, and the other end of the coil spring 80 bears against the spring stop 92 of the scale 90.

It can be seen from the above description that the adjusting wheel 64 and attached threaded sleeve 62 can be rotated relative to the rest of the cylinder apparatus 50. This rotation causes the threaded ring 70, which is prevented from rotating by the threaded ring tab 72 engaged in the read-out portion 94 of the scale 90, to thread along the threaded sleeve 62. The threaded ring moves down if the rotation is in one direction, and the threaded ring moves up if the rotation is in the other direction. Downward movement of the threaded ring compresses the coil spring 80 between the threaded ring and the spring stop 92 of the scale 90, thereby urging the hollow sleeve 56 out of the hollow cylinder 52 to lengthen the cylinder apparatus 50 and to lower the heel. The extent of the downward movement controls the amount of force applied to the heel. This force is quantified by the position of the threaded ring relative to the scale 90 as determined through the window 102.

When the invention is positioned on the patient and a spring force is selected by use of the adjusting wheel 64, it can bee seen that the selected force will gradually decrease as the coil spring 80 extends to push the hollow sleeve 56 out of the hollow cylinder 52 to lower the heel. As the force decreases as the hollow sleeve is pushed out of the hollow cylinder, the scale 90 will be carried with the hollow sleeve, thereby causing the scale to slide relative to the threaded ring 70. This sliding will cause the threaded ring to indicate a changed scale reading, corresponding to the changed force level. Of course, the initial design of the device may require calibrating the scale so that the force indications are accurate.

The overall length between the lower ball 36 and upper ball 137 is adjustable to accommodate patients of different sizes and application of the device in a variety of ways. The upper shaft 112 which terminates in the upper ball 137 fits inside the threaded sleeve 62 through a central hole in the adjusting wheel 64 and is slidable in relation thereto. One end of a bracket 126 is attached to and extends from the outer surface of the hollow cylinder 52 and around the adjusting wheel 64. The other end of the bracket 126 is attached to a split ring clamp 110 which extends around the upper shaft 122. A thumb screw or other screw 130 extends through the split ring clamp 110 to clamp or unclamp the split ring clamp from the upper shaft. A thumb wheel 132 is attached to the head of the screw to allow quick manual clamping and unclamping.

The length adjustment is accomplished by operating the thumb wheel 132 to unclamp the upper shaft 112 from the split ring clamp 110. The upper shaft can then slide in or out of the hollow cylinder 52 as desired for the chosen length. The thumb wheel 132 is then operated to re-clamp the upper shaft 112 to fix its position relative to the hollow cylinder 52.

Figure 6:
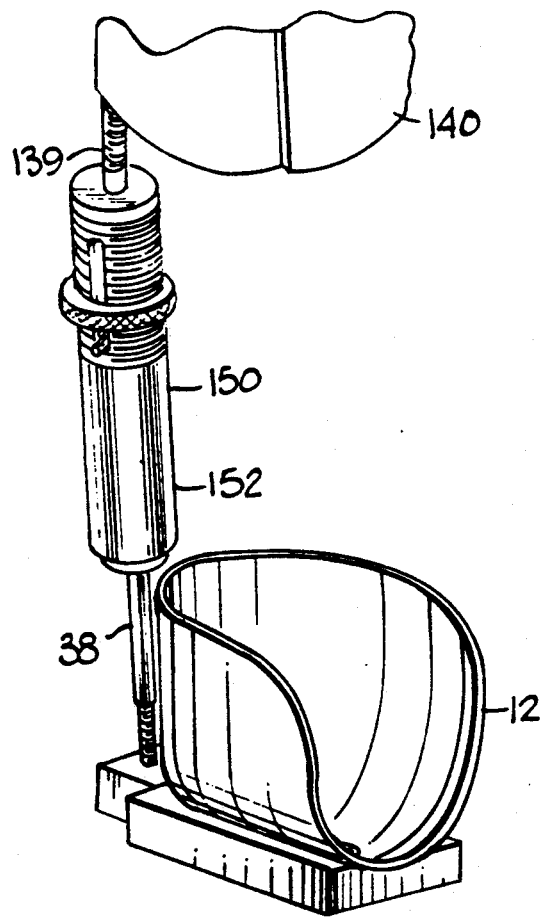
FIG. 6 shows a partial sectional view of the spring-filled cylinder and piston of the other embodiment configured for urging the lower leg and heel together.
Figure 7:
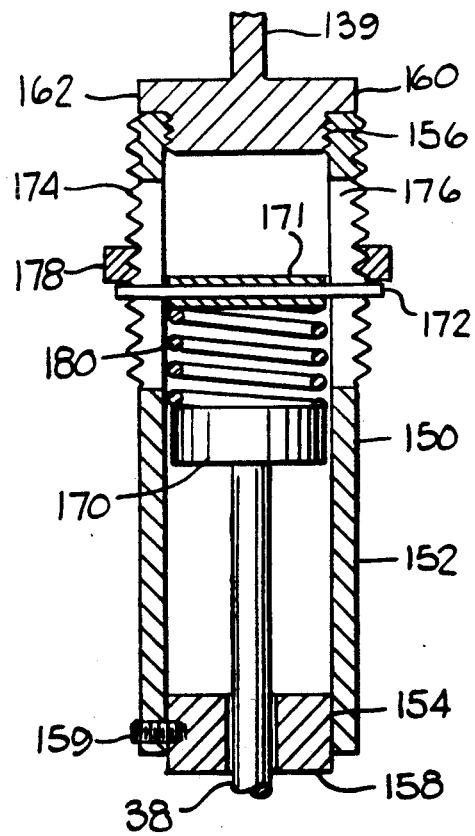
FIG. 7 shows a perspective view of the preferred embodiment of the present invention, equipped with a drive means to cyclically apply force between the lower leg and heel.
Figure 8:
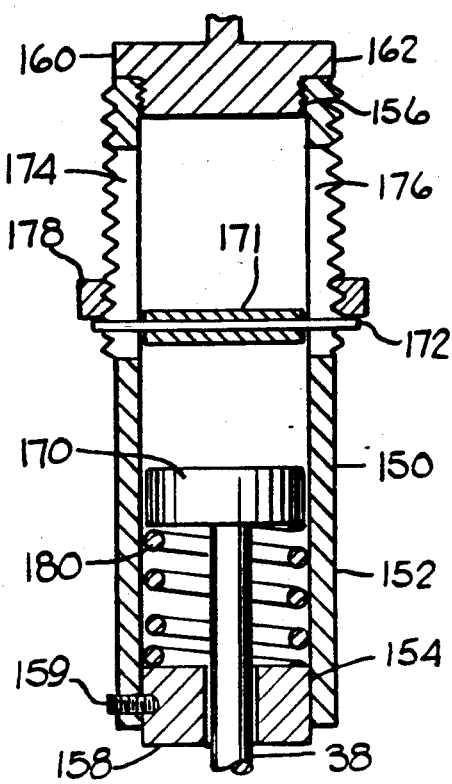

An alternative embodiment of the invention 10 is shown in FIGS. 6-8. As in the preferred embodiment, the alternative embodiment includes a heel cup 12 which attaches through a lower ball and socket (not shown) to a lower shaft 38. It also includes an upper shaft 139 which terminates in an upper ball 137 which engages an upper socket (not shown). The upper socket is attached to a lower leg cuff bracket (not shown) which is attached to the lower leg cuff 140.

The lower shaft 38 extends from the ball to the bottom of the spring-filled cylinder and piston arrangement 150. The spring-filled cylinder and piston arrangement 150 includes a cylinder 152 which is open at the bottom 154 and at the top 156. The open cylinder bottom 154 receives a cylinder bottom plug 158 which is slidably mounted on the lower shaft 38. The cylinder bottom plug 158 is fixed inside the open cylinder bottom 154 with a set screw 159 or other appropriate attachment means. The open cylinder top 156 threadably receives a cylinder top plug 160. The cylinder top plug 160 may be knurled on the exterior 162 to allow manual threading and unthreading from the cylinder open top 156.

Inside the cylinder 152 is a slidable piston 170 fixed at the end of the lower shaft 138. A cylindrical stopper 171 is slidably positioned between the piston 170 and the cylinder top plug 160. A stopper pin 172 is inserted through two slots 174 and 176 in opposite walls of the cylinder 152 so that the stopper pin 172 extends through the cylinder 152 and through the cylindrical stopper 171. A stopper adjustment 178 is threaded onto the outer surface of the cylinder 152 above the stopper pin 172 to limit the upward slidable movement of the stopper 171 and the stopper pin 172 through the slots 174 and 176. A spring 180 is compressed between the upper surface of the piston 170 and the stopper 171.

In operation, the compressed spring 180 urges the heel cup 12 away from the lower leg 17 by applying a force to the upper surface of the piston 170 and the lower surface of the stopper 171. As this force causes the gradual withdrawal of the piston 170 from the cylinder 152, the distance increases from the lower leg to the back of the heel. The resulting drop in the heel is accompanied by a pivoting of the foot through the ankle joint and a consequent lifting of the front of the foot. The balls and sockets allow this pivoting to occur about any combination of axes in any plane whatsoever that runs through the balls, thereby accommodating joint component motion.

The force exerted to urge the heel down from the lower leg is adjustable by threading the stopper adjustment 178 up or down the threaded exterior surface of the cylinder 152. As the stopper adjustment 178 is threaded downward, it slides the stopper 171 and the stopper pin 172 downward through the slots 174 and 176. This decreases the distance between the stopper 171 and the upper surface of the piston 170, thereby further compressing the spring 180 and increasing the force on the piston 170. Conversely, the stopper adjustment 178 may be threaded upward on the threaded exterior surface of the cylinder 152, thereby allowing the stopper 171 and the stopper pin 172 to slide upward in the slots 174 and 176 to lengthen the distance between the stopper 171 and the surface of the piston 170 to decrease the force on the piston 170. This varying force can be quantified by suitable alpha or numeric characters (not shown) on the exterior surface of the cylinder 152 to indicate the positioning of the stopper adjustment 178.

The force applied between the lower leg and heel can be changed from compression to tension or from tension to compression by changing the position of the spring 180 relative to the piston 170. If the spring 180 is positioned between the stopper 171 and the piston 170, then the spring 180 will urge the piston 170 out of the cylinder 152, thereby increasing the distance between the lower leg and the heel. If the spring 180 is positioned between the piston 170 and the cylinder bottom plug 158, then the spring 180 will urge the piston 170 into the cylinder, thereby shortening the distance between the lower leg and the heel.

This second configuration, shown in FIG. 8 is achieved by removing the cylinder top plug 160 from the cylinder 152, removing the spring 80 from the cylinder 152, removing the cylinder bottom plug 158 from the cylinder 152, placing the spring 180 into the bottom of the cylinder 152 so that it is positioned below and bear upon the lower surface of the piston 170, replacing the cylinder bottom plug 158 into the cylinder 152, and replacing the cylinder top plug 160 into the cylinder 152. This second configuration causes compression of the spring between the lower surface of the piston 170 and the upper surface of the cylinder bottom plug 158, to urge the piston into the cylinder, thereby decreasing the distance between the lower leg and heel.

The invention may also be configured to cyclically mobilize the joint by combining with a suitable drive mechanism in the manner shown in application No. 495,044 of which this is continuation-in-part. The drive mechanism of the apparatus includes a programmable stepper motor positioned on the lower leg cuff 140. The drive shaft of the stepper motor has end threads which threadably engage the upper shaft of the apparatus. The turning of the stepper motor drive shaft clockwise or counterclockwise by operating the stepper motor in forward and reverse, causes the end threads to thread in or out of the engagement in the upper shaft thread.

As will be apparent to those skilled in the art, other variations are possible without departing from the spirit of the invention. For example, rather than using a spring-biased force-applying means, a pneumatic or hydraulic force-applying means could be used. Rather than using a ball and socket to attach the heel cup and lower leg cuff to the force-applying means, universal type joints could be used with the same effect.

What is claimed is:

1. A method of increasing the mobility of an ankle joint, comprising:
   (a) attaching one end of a force-applying apparatus to the lower leg;
   (b) attaching the other end of the force-applying apparatus to the heel; and
   (c) applying a force between the heel and the lower leg to urge the heel away from the lower leg utilizing said force-applying apparatus;
   the force-applying apparatus having an expandable cylinder portion, a heel cup attached to the heel and pivotally attached to the lower end of said expandable cylinder portion, and a lower leg cuff attached to the lower leg and pivotally attached with pivotal attachment means to the upper end of the expandable cylinder;
   the expandable portion having an outer hollow cylinder with upper and lower ends, a first sleeve slidably engaged in said outer hollow cylinder with a lower end extending out of the lower end of said hollow cylinder, said lower end being attached to said pivotal attachment means, and force-applying means for urging said first sleeve out of said hollow cylinder.

2. The method of claim 1, wherein said force-applying means includes a coil spring with upper and lower ends.

3. The method of claim 2, wherein said coil spring is a compression spring and said force-applying means includes:
   (a) a lower spring stop which bears on the coil spring lower end and is attached to the first sleeve; and
   (b) an upper spring stop which bears on the coil spring upper end.

4. The method of claim 3, further comprising adjusting the amount of force urging the first sleeve out of the hollow cylinder utilizing a force-adjusting means.

5. The method of claim 4, wherein said force-adjusting means includes means for adjusting the position of said upper spring stop, thereby adjusting the compression of said spring.

6. The method of claim 5 wherein said means for adjusting the position of said upper spring stop includes:
   (a) a threaded second sleeve slidably engaged in said outer hollow cylinder with an upper end extending out of the upper end of said hollow cylinder;
   (b) an adjusting wheel attached to the upper end of and extending radially from the threaded second sleeve with a top and bottom side, the adjusting wheel being prevented from movement in the axial direction of the outer hollow cylinder by the outer hollow cylinder on the adjusting wheel bottom side and by a retaining means attached to the outer hollow cylinder on the adjusting wheel top side; and
   (c) threads on said upper spring stop to threadably engage said threaded second sleeve;
   (d) means for preventing the rotation of said upper spring stop, so that rotation of the adjusting wheel and threaded second sleeve causes adjustment of the position of said upper spring stop and the compression of said coil spring, by causing the spring stop to thread along the threaded second sleeve.

7. The method of claim 6, wherein said force-applying apparatus includes means for measuring the amount of force applied.

8. The method of claim 7, wherein said means for measuring the amount of force applied includes a scale attached to the first sleeve, said scale having force-indicating markings and extending axially along the outer hollow cylinder and slidably positioned in and visible through a window in the outer hollow cylinder.

9. The method of claim 8, wherein the means for preventing the rotation of said upper spring stop includes a tab on said upper spring stop that slidably engages a slot in said scale.

10. The method of claim 9, wherein the amount of force that is being applied is determined by examining the position of the upper spring stop relative to the scale and the markings thereon.

11. The method of claim 10, further comprising adjusting the distance between said heel cup and said lower leg using a distance adjustment apparatus.

12. The method of claim 11, wherein said distance adjustment apparatus includes:
   (a) an upper shaft connecting said lower leg cuff with said expandable cylinder, said upper shaft slidably engaged inside said threaded second sleeve;
   (b) releasable clamping means attached to said outer hollow cylinder to clamp the upper shaft to prevent axial movement of the upper shaft with respect to said outer hollow cylinder.

13. The method of claim 12, wherein said releasable clamping means includes:
   (a) a split collar slidably engaged on said upper shaft and attached to the outer hollow cylinder
   (b) a clamping crew through the collar and the split in the collar to clamp and release said split collar; and
   (c) means to cause screwing and unscrewing of the clamping screw.

14. An apparatus for increasing the mobility of the ankle joint, comprising:
   (a) a heel cup to receive a patient's heel;
   (b) a lower leg cuff to receive the patient's lower leg; and
   (c) an expandable cylinder portion having an outer hollow cylinder with an upper end and a lower end, force-applying means located inside said outer hollow cylinder to apply a force between said heel cup and said lower leg cuff, and first force-transmitting means to transmit said force form said force-applying means to said heel cup;
   (d) means for attaching said heel cup to said expandable cylinder portion; and
   (e) means for attaching said lower leg cuff to said expandable cylinder portion.

15. The apparatus of claim 14, wherein:
   (a) said outer hollow cylinder has a hole in the lower end in a radial plane of said outer hollow cylinder;
   (b) said force-applying means includes a coil spring positioned in the interior of said outer hollow cylinder; and
   (c) said first force-transmitting means includes a first force-transmitting shaft slidably mounted in said lower end hole to so that a portion is in the interior of the outer hollow cylinder, to receive the force applied by said coil spring.

16. The apparatus of claim 15, wherein said first force-transmitting shaft includes a first sleeve in the portion of the first force-transmitting shaft that is in the interior of the outer hollow cylinder.

17. The apparatus of claim 16, further comprising means for adjusting the amount of force applied by said force-applying means.

18. The apparatus of claim 17, wherein said force applying means is a coil compression spring with a lower and an upper end.

19. The apparatus of claim 18, further comprising:
   (a) a lower spring stop mounted on said first sleeve to bear against the lower end of the coil spring and to transmit force from the coil spring to the first sleeve; and
   (b) an upper spring stop to bear against the upper end of said coil spring.

20. The apparatus of claim 19, further comprising:
   (a) means for preventing the rotation of said upper spring stop in a radial plane of said outer hollow cylinder; and
   (b) a threaded shaft rotatably mounted inside said first sleeve, and wherein said upper spring stop is threaded onto said threaded shaft so that rotating said threaded shaft causes threaded movement of said upper spring stop relative to said threaded shaft.

21. The apparatus of claim 20, wherein said outer hollow cylinder has a window extending in the longitudinal direction, from the exterior through to the interior; and further comprising a scale attached to said first hollow sleeve and extending longitudinally and nesting in said outer hollow cylinder window, said scale having markings to indicate the amount of force applied between the heel cup and lower leg.

22. The apparatus of claim 21, wherein said means for preventing the rotation of the upper spring stop is a tab on the upper spring stop and a tab-engaging slot in the longitudinal direction of said scale, so that rotation of the threaded shaft causes the upper spring stop to thread along the threaded shaft and the tab to slide along the tab-engaging slot, so that the position of the upper spring slot relative to the scale and force-indicating scale markings is visible through the window to determine the amount of force applied between the heel cup and lower leg cuff.

23. The apparatus of claim 14, further comprising second force-transmitting means to transmit said force from said force applying means to said lower leg cuff.

24. The apparatus of claim 23, wherein said second force-transmitting means includes a second force-transmitting shaft the lower end of which is releaseably attached to said expandable cylinder portion and the upper end of which is attached to said means for attaching the lower leg cuff to the expandable cylinder portion, and further comprising means for releaseably attaching said second force-transmitting shaft to the expandable cylinder.

25. The apparatus of claim 24, wherein said means for attaching said second force-transmitting shaft to said expandable cylinder is a releasable clamp attached to the outer hollow cylinder and clamped to the second force-transmitting shaft.

26. A method of increasing the mobility of an ankle joint, comprising:
   (a) attaching one end of a force-applying apparatus to the lower leg;
   (b) attaching the other end of the force-applying apparatus to the heel, the force applying apparatus including an expandable cylinder portion, a heel cup attachable to the heel and pivotally attached to the lower end of said expandable cylinder portion, and a lower leg cuff attachable to the lower leg and pivotally attached with pivotal attachment means to the upper end of the expandable cylinder; and
   cylically flexing and extending the joint by cyclical application of said force including a force urging the heel away from the lower leg, and wherein said cyclical application is by a programmable stepper motor which is cooperatively engaged with said expandable cylinder portion and which cycles through a forward mode and reverse mode.

27. The method of claim 26, wherein said stepper motor lengthens and shortens the distance between the heel and the lower leg by threading the stepper motor shaft forward and backward through a threaded motor shaft engagement attached to said apparatus.

28. An apparatus for increasing the mobility of the ankle joint, comprising:
   (a) an expandable cylinder portion;
   (b) a heel cup to receive a patient's heel;
   (c) means for attaching said heel cup to said expandable cylinder portion;
   (d) a lower leg cuff to receive the patient's lower leg;
   (e) means for attaching said lower leg cuff to said expandable cylinder portion; and
   (f) drive means attached t said apparatus for cylically increasing and decreasing the distance between the heel cup and lower leg cuff.

29. The apparatus of claim 28, wherein said drive means is a programmable stepper motor.

30. The apparatus of claim 29, wherein said stepper motor is attached to one of the heel cup and lower leg cuff and has a threaded shaft which threadably engages a threaded engagement attached to the expandable cylinder portion, so that operating the stepper motor in the forward and reverse modes causes the shaft to thread in and out of the threaded engagement, thereby lengthening and shortening the distance between the heel cup and lower leg cuff.

* * * * *